(12) United States Patent
Ishihara et al.

(10) Patent No.: US 11,529,200 B2
(45) Date of Patent: Dec. 20, 2022

(54) REMOTE CONTROL APPARATUS AND REMOTE CONTROL SYSTEM

(71) Applicant: MEDICAROID CORPORATION, Kobe (JP)

(72) Inventors: Kazuki Ishihara, Kobe (JP); Tetsuya Nakanishi, Kobe (JP); Shiro Horita, Kobe (JP)

(73) Assignee: MEDICARON CORPORATION, Kobe (JP)

( * ) Notice: Subject to any disclaimer, the term of this patent is extended or adjusted under 35 U.S.C. 154(b) by 324 days.

(21) Appl. No.: 16/699,735

(22) Filed: Dec. 2, 2019

(65) Prior Publication Data
US 2020/0100852 A1 Apr. 2, 2020

Related U.S. Application Data

(63) Continuation of application No. PCT/JP2018/021844, filed on Jun. 7, 2018.

(30) Foreign Application Priority Data

Jun. 8, 2017 (JP) .............................. JP2017-113304

(51) Int. Cl.
*A61B 34/00* (2016.01)
*A61B 34/35* (2016.01)
(Continued)

(52) U.S. Cl.
CPC ............ *A61B 34/25* (2016.02); *A61B 17/221* (2013.01); *A61B 17/29* (2013.01); *A61B 18/148* (2013.01);
(Continued)

(58) Field of Classification Search
CPC ... A61B 34/25; A61B 2034/258; A61B 34/35; A61B 90/60; A61B 17/221; A61B 17/29;
(Continued)

(56) References Cited

U.S. PATENT DOCUMENTS

| | | | |
|---|---|---|---|
| 6,436,107 B1 | 8/2002 | Wang et al. | |
| 2003/0220564 A1* | 11/2003 | Wilkins | F16M 11/046 600/437 |

(Continued)

FOREIGN PATENT DOCUMENTS

| | | |
|---|---|---|
| EP | 2092892 A1 | 8/2009 |
| EP | 3184069 A1 | 6/2017 |

(Continued)

*Primary Examiner* — Aaron F Roane
(74) *Attorney, Agent, or Firm* — Metrolex IP Law Group, PLLC

(57) ABSTRACT

A remote control apparatus according to one or more embodiments may include a display, an operation handle, an armrest, and a supporting mechanism. The supporting mechanism includes a supporting section that supports the display, the operation handle, and the armrest and a driver configured to move the supporting section in an up-and-down direction. The supporting mechanism is configured, upon transitioning between a first mode and a second mode, to move the supporting section by the driver in the up-and-down direction to move the display, the operation handle, and the armrest in an integrated manner in the up-and-down direction.

23 Claims, 10 Drawing Sheets

(51) Int. Cl.
*A61B 90/60* (2016.01)
*A61B 17/221* (2006.01)
*A61B 17/29* (2006.01)
*A61B 18/14* (2006.01)
*H04N 7/18* (2006.01)

(52) U.S. Cl.
CPC .............. *A61B 34/35* (2016.02); *A61B 90/60* (2016.02); *H04N 7/183* (2013.01); *A61B 2018/1412* (2013.01)

(58) Field of Classification Search
CPC .......... A61B 18/148; A61B 2018/1412; H04N 7/183
USPC .......................................................... 606/1
See application file for complete search history.

(56) References Cited

U.S. PATENT DOCUMENTS

| | | | |
|---|---|---|---|
| 2010/0152588 A1* | 6/2010 | Ninomiya | G01S 7/52082 600/459 |
| 2010/0225209 A1 | 9/2010 | Goldberg et al. | |
| 2011/0087238 A1 | 4/2011 | Wang et al. | |
| 2011/0118748 A1* | 5/2011 | Itkowitz | A61B 34/37 606/130 |
| 2014/0195010 A1 | 7/2014 | Beira et al. | |
| 2015/0038981 A1 | 2/2015 | Kilroy et al. | |
| 2015/0038984 A1 | 2/2015 | Hiroe et al. | |
| 2015/0157410 A1 | 6/2015 | Kilroy et al. | |
| 2015/0238073 A1 | 8/2015 | Charles et al. | |
| 2015/0265807 A1* | 9/2015 | Park | A61B 5/06 600/424 |
| 2016/0374771 A1 | 12/2016 | Mirbagheri et al. | |
| 2017/0165014 A1* | 6/2017 | Nakanishi | A61B 34/74 |

FOREIGN PATENT DOCUMENTS

| | | |
|---|---|---|
| JP | 2002-537884 A | 11/2002 |
| JP | 2004-337443 A | 12/2004 |
| JP | 2008-126015 A | 6/2008 |
| JP | 2013-510671 A | 3/2013 |
| JP | 2013-255736 A | 12/2013 |
| JP | 2015-521913 A | 8/2015 |
| JP | 2016-519585 A | 7/2016 |
| JP | 2017-104455 A | 6/2017 |
| WO | 2014/151621 A1 | 9/2014 |
| WO | 2018/057814 A1 | 3/2018 |

* cited by examiner

FIXED STATE

UNLOCK STATE

DETACHED STATE

FIXED STATE

UNLOCK STATE

DETACHED STATE

FIXED STATE

UNLOCK STATE

DETACHED STATE

REMOTE CONTROL APPARATUS AND REMOTE CONTROL SYSTEM

CROSS REFERENCE TO RELATED APPLICATIONS

This application is a continuation application of International Application No. PCT/JP2018/021844 filed on Jun. 7, 2018, which claims priority to Japanese Patent Application No. 2017-113304 filed on Jun. 8, 2017, the entire contents of each of which are incorporated herein by reference.

BACKGROUND

The disclosure may relate to a remote control apparatus and a remote control system and, more specifically, relate to a remote control apparatus and a remote control system to control medical equipment.

In a related art, a remote control apparatus to control medical equipment is known. For example, U.S. Patent Application Publication No. 2011/0087238 discloses a minimally invasive surgical system that includes a cabinet including a handle to be operated in a standing position. In the minimally invasive surgical system disclosed in U.S. Patent Application Publication No. 2011/0087238, an operator operates a surgical manipulator (medical equipment) by operating the handle in the standing position. Further, U.S. Patent Application Publication No. 2014/0195010 includes a handle that is to be operated in a sitting position, so that the operator in the sitting position operates an end effector of a surgical manipulator by operating the handle. In the control apparatus for the surgical manipulator disclosed in U.S. Patent Application Publication No. 2011/0087238 and U.S. Patent Application Publication No. 2014/0195010, the operator is required to operate the handle in only either of the standing position or the sitting position. Thus, in some cases, the operator cannot take desired postures. On the other hand, International Application Publication No. WO2014/151621 discloses a remote control apparatus for a surgical manipulator using a wireless handheld portable input device. Since the remote control apparatus of International Application Publication No.

WO2014/151621 has portability, it is possible to operate the control apparatus in a standing position and a sitting position.

SUMMARY

However, in the control apparatus for the medical manipulator disclosed in International Application Publication No. WO2014/151621, even though the operator can operate the control apparatus in the standing position and the sitting position, the operator is required to hold the control apparatus, which increases the burden on the operator. Therefore, there is a problem in that it is difficult to allow the operator to operate the remote control apparatus in desired postures while suppressing an increase of the burden on the operator.

An object of an embodiment of the disclosure may be to provide a remote control apparatus and a remote control system that allow an operator to operate in desired postures while suppressing an increase of a burden on the operator.

A remote control apparatus according to an aspect of the disclosure may include: a display configured to display an image captured by an endoscope; an operation handle configured to be movable within a predetermined operation range and to remotely operate medical equipment; an armrest to support arms of an operator; and a supporting mechanism that includes a supporting section supporting the display, the operation handle, and the armrest and a driver configured to move the supporting section in an up-and-down direction, wherein the supporting mechanism is configured to be transitionable between a first mode in which the operation handle that is positioned at a neutral position of the operation range is held at a first height position, which is 85 cm or more above a floor surface on which the remote control apparatus is placed and a second mode in which the operation handle that is positioned at the neutral position of the operation range is held at a second height position, which is 48 cm or more below the first height position. The supporting mechanism moves, upon transitioning between the first mode and the second mode, the supporting section in the up-and-down direction by the driver to move the display, the operation handle, and the armrest in an integrated manner in the up-and-down direction.

A remote control apparatus according to another aspect of the disclosure may include: a display configured to display an image captured by an endoscope; an operation handle configured to be movable within a predetermined operation range and to remotely operate medical equipment; an armrest to support arms of an operator; and a supporting mechanism that includes a supporting section supporting the display, the operation handle, and the armrest and a driver configured to move the supporting section in an up-and-down direction, wherein the supporting mechanism is configured to be transitionable between a first mode in which the operation handle is held such that the operation range of the operation handle is within in a clean area set at a predetermined height position or more above a floor surface on which the remote control apparatus is placed, and a second mode in which the operation handles are held such that at least a part of the operation range of the operation handle is located below the clean area. The supporting mechanism moves, upon transitioning between the first mode and the second mode, the supporting section in the up-and-down direction by the driver to move the display, the operation handle, and the armrest in an integrated manner in the up-and-down direction.

A remote control apparatus according to still another aspect of the disclosure may include: a display configured to display an image captured by an endoscope; an operation handle configured to be movable within a predetermined operation range and to remotely operate medical equipment; an armrest to support arms of an operator; and a supporting mechanism that includes a supporting section supporting the display, the operation handle, and the armrest and a driver configured to move the supporting section in an up-and-down direction, wherein the supporting mechanism is configured to be transitionable between a first mode in which the operation handle is held at a position suitable for the operator to operate the operation handle at a standing posture and a second mode in which the operation handle is held at a position suitable for the operator to operate the operation handle in a sitting posture. The supporting mechanism moves, upon transitioning between the first mode and the second mode, the supporting section in the up-and-down direction by the driver to move the display, the operation handle, and the armrest in an integrated manner in the up-and-down direction.

BRIEF DESCRIPTION OF DRAWINGS

FIGS. 8A to 8C are schematic views for explaining a first example of a lock mechanism and an unlock mechanism of the remote control apparatus according to a first embodiment, wherein FIG. 8A illustrates a fixed state of the first example, FIG. 8B illustrates an unlocked state of the first example, and FIG. 8C illustrates a detached state of the first example;

FIGS. 9A to 9C are schematic views for explaining a second example of a lock mechanism and an unlock mechanism of the remote control apparatus according to a first embodiment, wherein FIG. 9A illustrates a fixed state of the second example, FIG. 9B illustrates an unlocked state of the second example, and FIG. 9C illustrates a detached state of the second example;

FIGS. 10A to 10C are schematic views for explaining a third example of a lock mechanism and an unlock mechanism of the remote control apparatus according to a first embodiment, wherein FIG. 10A illustrates a fixed state of the third example, FIG. 10B illustrates an unlocked state of the third example, and FIG. 10C illustrates a detached state of the third example;

DETAILED DESCRIPTION

Embodiments are explained with reference to drawings hereinafter.

First Embodiment

[Configuration of Remote Control Apparatus]

A configuration of a remote control apparatus 100 according to a first embodiment is described with reference to FIGS. 1 to 10C.

Figure 1:
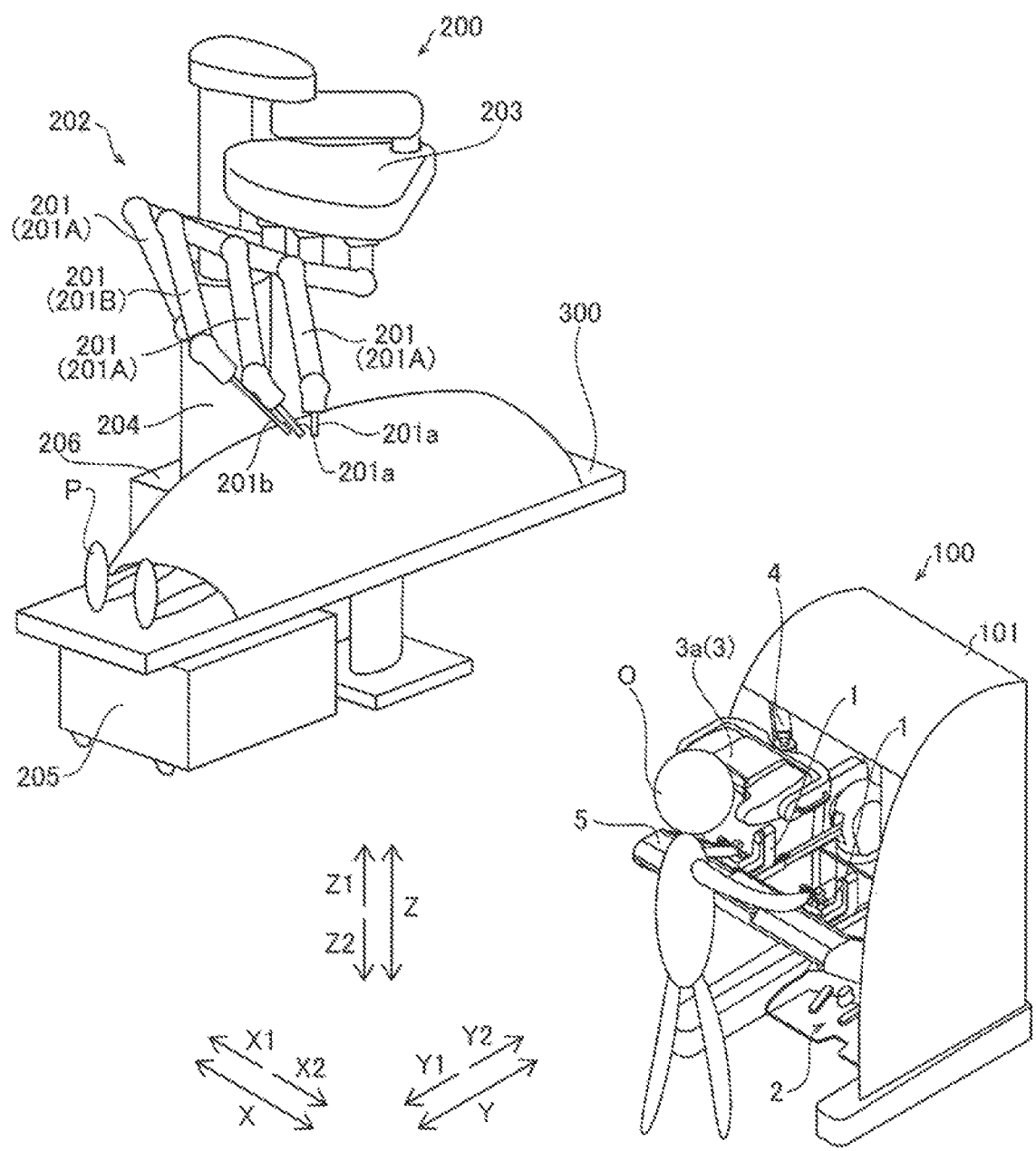
FIG. 1 is a schematic view illustrating a remote control apparatus according to a first embodiment.

As illustrated in FIG. 1, the remote control apparatus 100 is provided for teleoperation of medical equipment included in a patient-side system 200. When an operator O, as a surgeon, inputs an action mode instruction to be executed by the patient-side system 200, to the remote control apparatus 100, the remote control apparatus 100 transmits the action mode instruction to the patient-side system 200 through a controller 206. In response to the action mode instruction transmitted from the remote control apparatus 100, the patient-side system 200 operates medical equipment, such as surgical instruments, an endoscope, and the like, held by surgical manipulators 201. This allows for minimally invasive surgery. A surgery assisting system includes the remote control apparatus 100 and the patient-side system 200 including the surgical manipulators 201.

The patient-side system 200 constitutes an interface to perform a surgery for a patient P. The patient-side system 200 is placed beside an operation table 300 on which the patient P lies. The patient-side system 200 includes the plural surgical manipulators 201. One of the surgical manipulators 201 holds an endoscope 201b while the others hold surgical equipment (instruments 201a). The surgical manipulator 201 holding surgical instruments (instruments 201a) function as instrument arms 201A while the surgical manipulator 201 holding the endoscope 201b functions as a camera arm 201B. The instrument arms 201A and camera arm 201B are commonly supported by a platform 203. Each of the surgical manipulators 201 includes plural joints. Each joint includes a driver including a servo-motor and a position detector such as an encoder. The surgical manipulators 201 are configured so that medical equipment attached to each surgical manipulator 201 is controlled by a driving signal given through the controller 206, to perform a desired movement.

The platform 203 is supported by a positioner 202 placed on a floor of an operation room. The positioner 202 includes a column 204 and a base 205. The column 204 includes an elevating shaft adjustable in the vertical direction. The base 205 includes wheels and is movable on the floor surface.

The instrument arms 201A detachably hold the instruments 201a as the medical equipment at distal end portions thereof. Each instrument 201a includes a housing attached to the instrument arm 201A and an end effector provided at a distal end of an elongated shaft. An example of the end effector is grasping forceps, a hook, scissors, a high-frequency knife, a snare wire, a clamp, or a stapler, but is not limited to those and can be various types of treatment tools. In surgeries using the patient-side system 200, the instrument arms 201A are introduced into a body of a patient P through a cannula (trocar) placed on the body surface of the patient P, and the end effector of each instrument 201a is located near the surgery site.

To a distal end portion of the camera arm 201B, the endoscope 201b (see FIG. 3), as the medical equipment, is detachably attached. The endoscope 201b captures an image within the body cavity of the patient P. The captured image is outputted to the remote control apparatus 100. A 3D endoscope capable of capturing a three-dimensional image or a 2D endoscope is used as the endoscope 201b. In surgeries using the patient-side system 200, the camera arm 201B is introduced into the body of the patient P through a trocar placed on the body surface of the patient P, and the endoscope 201b is located near the surgery site.

The remote control apparatus 100 constitutes an interface with the operator O. The remote control apparatus 100 is an apparatus that allows the operator O to operate medical equipment held by the surgical manipulators 201. Specifically, the remote control apparatus 100 is configured to transmit action mode instructions which are inputted by the operator O and are to be executed by the instruments 201a and endoscope 201b, to the patient-side system 200 through the controller 206. The remote control apparatus 100 is installed beside the operation table 300 so that the operator O can see a state of the patient P very well while operating the master apparatus, for example. The remote control apparatus 100 may be configured to transmit the action mode instructions wirelessly and installed in a room different from the operation room in which the operation table 300 is installed.

The action modes to be executed by the instruments 201*a* include a mode of actions (a series of positions and postures) to be taken by each instrument 201*a* and actions to be executed by the function of each instrument 201*a*. For example, in a case where the instrument 201*a* is a pair of grasping forceps, the action mode to be executed by the instrument 201*a* may include roll and pitch positioning of the wrist of the end effector and the action to open or close the jaws. For example, in a case where the instrument 201*a* is a high-frequency knife, the action mode to be executed by the instrument 201*a* may include vibration of the high-frequency knife, specifically, supply of current to the high-frequency knife. For example, in a case where the instrument 201*a* is a snare wire, the action mode to be executed by the instrument 201*a* may include a capturing action and an action to release the captured object, and may include an action to supply current to a bipolar or monopolar instrument to burn off the surgery site.

The action mode to be executed by the endoscope 201*b* includes the position and posture of the distal end of the endoscope 201*b* or setting of the zoom magnification, for example.

As illustrated in FIG. 1, the remote control apparatus 100 is provided with a cover 101. The cover 101 covers sides of the remote control apparatus 100 in the right and left direction (X direction), in the rear direction (Y2 direction), and in the upper direction (Z1 direction). Note that FIGS. 2 to 13 illustrate the remote control apparatus 100 in a state where the cover 101 is removed for descriptive purposes. for convenience.

Figure 2:
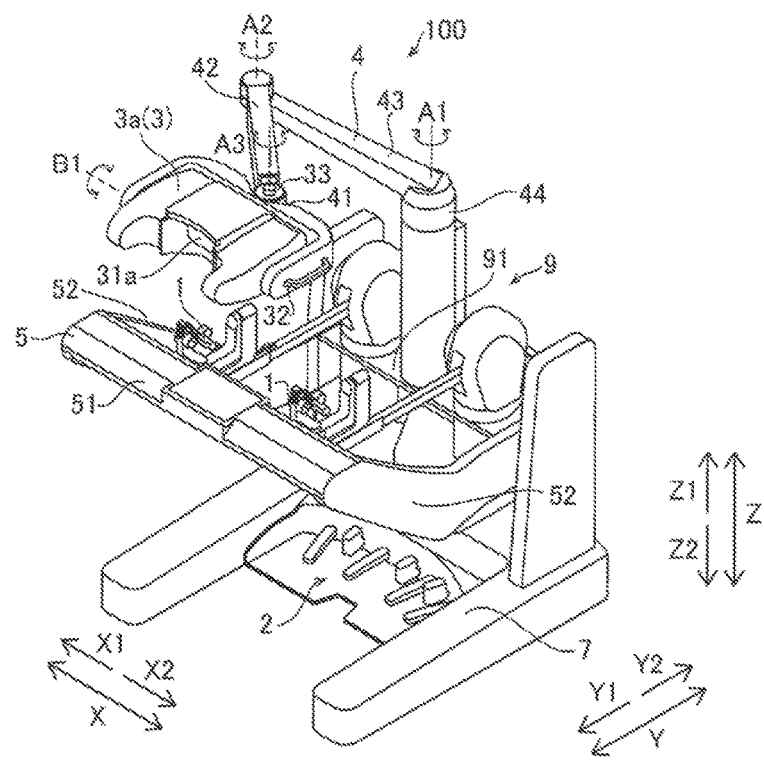
FIG. 2 is a view of the remote control apparatus t according to a first embodiment with a scope type display mounted thereon.
Figure 3:
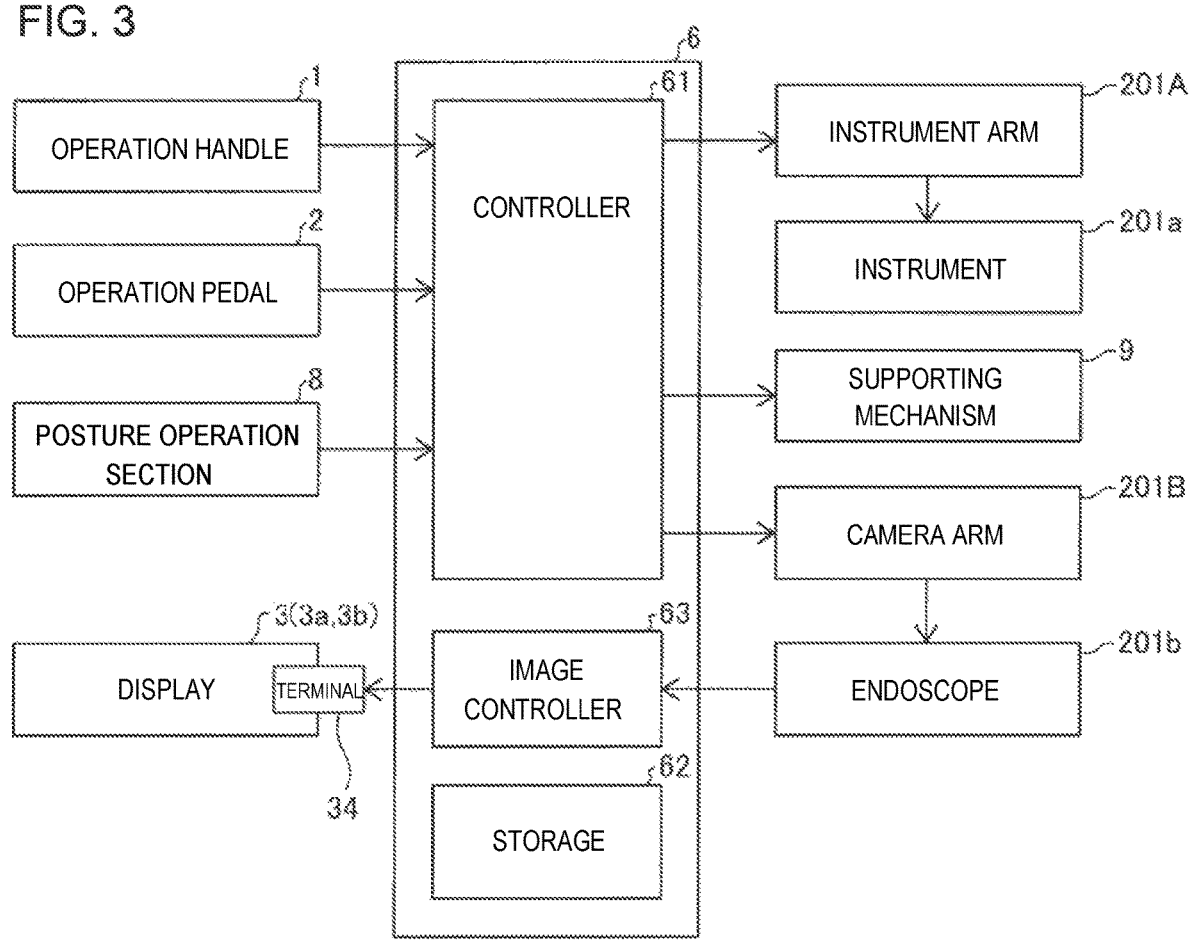
FIG. 3 is a block diagram illustrating a control-related configuration of the remote control apparatus according to a first embodiment.

As illustrated in FIGS. 2 and 3, the remote control apparatus 100 includes operation handles 1, an operation pedal 2, a display supporting arm 4 to support a display 3, an armrest 5 to support arms of the operator O, and a control apparatus 6, and a base 7. The remote control apparatus 100 further includes a posture operation section 8 and a supporting mechanism 9. The supporting mechanism 9 supports the operation handles 1 and armrest 5.

The operation handles 1 are provided in order to remotely operate medical equipment held by the surgical manipulators 201. Specifically, the operation handles 1 accept operations by the operator O for operating medical equipment (the instruments 201*a* and endoscope 201*b*). The operation handles 1 include a pair of operation handles 1 arranged side by side in the X direction. The operation handle 1 on the X2 side (on the right side) of the pair of operation handles 1 is operated by the right hand of the operator O while the operation handle 1 on the X1 side (on the left side) is operated by the left hand of the operator O.

The operation handles 1 are attached to a supporting section 91 of the supporting mechanism 9. The operation handles 1 are arranged extending from the back side (the Y2 side) toward the front side (the Y1 side) of the remote control apparatus 100. Plural joints are provided between the supporting section 91 and each operation handle 1 so that the operation handles 1 can move relative to the supporting section 91 in a predetermined three-dimensional operation range A (see FIGS. 4 and 5). Specifically, the operation handles 1 are configured so as to move relative to the supporting section 91, up and down (in the Z direction), right and left (in the X direction), and forward and backward (in the Y direction). Each joint between the supporting section 91 and the operation handles 1 is provided with a not-illustrated position detector that detects the positional relationship between the joints. The position detector is an encoder, a resolver, or a potentiometer, for example. The position detector thereby detects the positions of the operation handles 1 relative to the supporting section 91.

The remote control apparatus 100 and patient-side system 200 constitute a master-slave system in terms of controlling motion of the instrument arms 201A and camera arm 201B. That is, the operation handles 1 constitute an operating part on the master side in the master-slave system, while the instrument arms 201A and the camera arm 201B grasping medical equipment constitute movement parts on the slave side. When the operator O operates the operation handles 1, the motion of the instrument arms 201A or camera arm 201B is controlled so that the distal end parts (the end effectors of the instruments 201*a*) of the instrument arms 201A and the distal end part (the endoscope 201*b*) of the camera arm 201B move following the movement of the operation handles 1.

The patient-side system 200 controls the motion of the instrument arms 201A in accordance with the set motion scaling ratio. When the motion scaling ratio is set to 1/2, for example, the end effectors of the instruments 201*a* move 1/2 of the movement distance of the operation handles 1. This allows for precise fine surgery. The operation handles 1 are attached to the base 7 and extend toward the operator O in the Y direction.

The operation pedal 2 includes pedals to be operable by the foot of the operator O. A specific function is assigned to each pedal. One of the functions is to input a switching instruction to switch an object to be controlled by the operation handles 1 among the instrument arms 201A and the camera arm 201B. Thus, when the operator wants to change a field of view during surgery, the operator operates the operation pedal 2 to change the object to be controlled by the operation handle 1 from the instrument arm 201A to the camera arm 201B, so that the operator can move the endoscope 201*b* by operating the operation handle 1. After moving the endoscope 201*b*, the operator can operate the operation pedal 2 again to change the object to be controlled by the operation handle 1 from the camera arm 201B to the instrument arm 201A, so that the operator can return to continue the surgery. The operation pedal 2 is provided at a lower position where the operator can operate by the foot. The operation pedal 2 is configured to be movable in the Y direction.

Another function of the operation pedal 2 is to input an instruction for operations of the instruments 201*a* attached to the distal ends of the instrument arms 201A. For example, the operation pedal 2 can input an operation to cut the surgery site or coagulate the surgery site by the instrument 201*a*. For example, a voltage for cutting or a voltage for coagulating is applied to the instrument 201*a* by operating the operation pedal 2.

Figure 7:
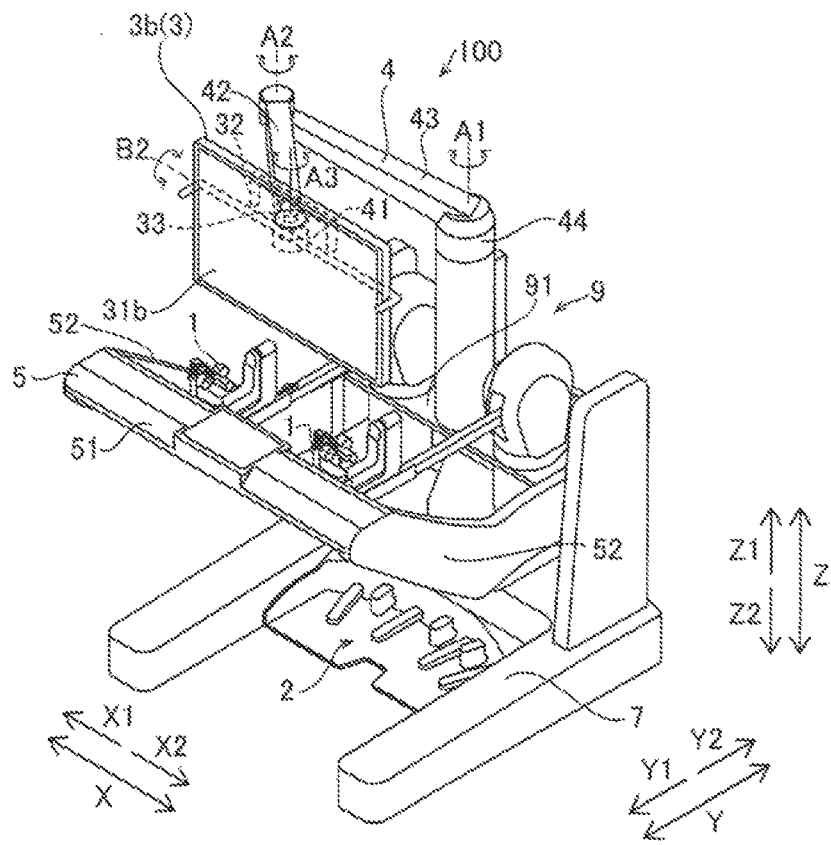
FIG. 7 is a view of the remote control apparatus according to a first embodiment with a non-scope type display mounted thereon.

The display 3 displays an image captured by the endoscope 201*b*. The display 3 may be a scope type display 3*a* or a non-scope type display 3*b*. The scope type display 3*a* is a display that the operator O looks into, for example. The non-scope type display 3*b* is a display including an open-type display that the operator O looks at without looking into and that has a flat screen, like a normal personal computer display. The scope and non-scope type displays 3*a* and 3*b* are selectively attachable to the remote control apparatus 100. Specifically, as illustrated in FIG. 2, the scope type display 3*a* includes a display 31*a*, a grip section 32, and an attachment section 33. As illustrated in FIG. 7, the non-scope type display 3*b* includes a display 31*b*, a grip section 32, and an attachment section 33. The attachment section 33 of the scope or non-scope type display 3*a* or 3*b* is attachable to the mounting section 41 of the display supporting arm 4 of the remote control apparatus 100. In other words, the scope or non-scope type display 3a or 3b mounted on the remote control apparatus 100 is configured to be supported by the display supporting arm 4. This allows the remote control apparatus 100 to be used as either an immersive remote control apparatus or an open-type remote control apparatus. Thus, the remote control apparatus 100 is versatile in terms of the display 3.

Surgery often takes several hours. Surgeons who work for a long time with an immersive remote control apparatus sometimes experience a sense of isolation. Switching the remote control apparatus 100 to an open-type remote control apparatus before or during surgery can make surgeons more likely to have a sense of performing the surgery within a team.

Further since the display of the remote control apparatus is versatile and expandable, if the display is broken or damaged, it is only necessary to repair the display and it is unnecessary to replace the entire apparatus. Moreover, the display can be upgraded without replacing the entire apparatus each time a higher definition or a higher quality display is developed. The operator can select a display of a favorite maker and favorite specifications (size, shape, type of operation panel, and the like).

The display 3 include a terminal 34 as illustrated in FIG. 3. The terminal 34 includes a terminal capable of transmitting video, such as a serial digital interface (SDI) terminal, an analogue component terminal, a high-definition multimedia interface (HDMI, registered trademark) terminal, or a universal serial bus (USB) terminal. The terminal 34 is connected to the control apparatus 6. By connecting connection wire to the terminal 34, the display 3 receives image information from the control apparatus 6. By disconnecting the connection wire from the terminal 34, the display 3 can be detached from the remote control apparatus 100.

When the scope type display 3a is attached, 3D image captured by the endoscope 201b held by the camera arm 201B of the patient-side system 200 is displayed on the scope type display 3a. When the non-scope type display 3b is attached, 3D image captured by the endoscope 201b provided to the patient-side system 200 is displayed on the non-scope type display 3b. Note that in a case where the non-scope type display 3b is attached, 2D image captured by the endoscope 201b provided to the patient-side system 200 may be displayed on the non-scope type display 3b.

The scope type display 3a is a viewer that the operator O looks into. The scope type display 3a displays an image for the right eye and an image for the left eye of the operator O. The scope type display 3a is a stereoscope, for example. The display 31a includes a display for the right eye and a display for the left eye. When the operator O is looking into the display 31a, the display for the right eye cannot seen by the left eye while the display for the left eye cannot be seen by the right eye. The display 31a is composed of a liquid crystal display, an organic EL display, or the like. The display 31a may be a projection-type display.

The non-scope type display 3b is an open-type display that the operator O is able to see without looking into. The non-scope type display 3b is a direct-view-type display. The display 31b of the non-scope type display 3b includes a flat or curved screen. The display 31b can be a display with a diagonal of 10 to 90 inches, for example. Considering the balance between sufficient visibility of the surgical field and easy replacement, the display 31b suitably has a diagonal of 15 to 30 inches. The display 31b is composed of a liquid crystal display, an organic EL display, or the like. The display 31b can be a projection-type display. The non-scope type display 3b may employ a publicly-known stereoscopy in order for the operator O to stereoscopically view an image captured by the endoscope 201b, such as a method using polarization glasses or a method using active shutter glasses.

The grip section 32 is gripped when the display 3 is mounted, dismounted, or moved. The grip section 32 can be gripped with one hand. The grip section 32 has a grip, recessed, protrusion shape, or the like, for example. The grip section 32 is provided on a lateral side or back side of the display 3 so as not to interfere with viewing the display 31a (31b). The grip section 32 can be gripped with one hand, and the grip section 32 may include plural grip sections 32. For example, the grip sections 32 may be provided on both sides of the display 3 as illustrated in FIG. 2, for example, so that the operator O sitting in front of the display 3 can grip any grip section 32 with either the right or left hand.

Figure 8A:
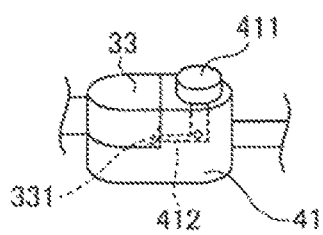
Figure 8B:
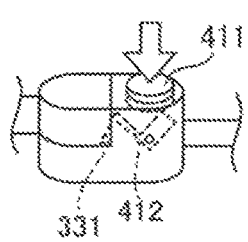
Figure 8C:
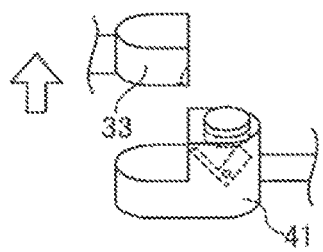

The attachment section 33 is attached to the mounting section 41 of the display supporting arm 4. That is, the mounting section 41 is detachably attached selectively to the scope or non-scope type display 3a or 3b. For example, the attachment section 33 includes an engagement section 331 as illustrated in FIGS. 8A to 8C as a first example. The mounting section 41 includes a lock release button 411 and an engagement section 412. As illustrated in FIG. 8A, in a fixed state, the engagement section 331 of the attachment section 33 is engaged with the engagement section 412 of the mounting section 41, so that the attachment section 33 is locked to the mounting section 41 of the display supporting arm 4. The display 3 is thereby fixed and supported by the display supporting arm 4. In other words, the engagement sections 331 and 412 constitute a lock mechanism to fix the display 3 (the scope or non-scope type display 3a or 3b).

As illustrated in FIG. 8B, when the lock release button 411 is pressed down, the engagement section 412 moves and disengages from the engagement section 331. Thus, the fixed state (the locked state) of the attachment section 33 with respect to the mounting section 41 is released. That is, the lock release button 411 functions as a lock release mechanism that releases the fixed state by the lock mechanism composed of the engagement sections 331 and 412. The lock release mechanism is configured to release the fixed state by the lock mechanism, with a force downward in the vertical direction. The lock release mechanism thereby easily releases the fixed state by the lock mechanism.

As illustrated in FIG. 8C, the grip section 32 of the display 3 is operated upward in the vertical direction while the lock release mechanism is acting downward in the vertical direction, so that the display 3 is dismounted from the remote control apparatus 100. In such a manner, the display 3 is dismounted by performing the releasing operation downward in the vertical direction and the operation of raising the grip section upward in the vertical direction, that produce forces in the opposite directions. The display 3 is therefore dismounted stably and safely. The display 3 is dismounted by being moved away from the display supporting arm 4 in the upward direction, thus the display 3 can be dismounted without being interfered with the operation handles 1 located underneath.

Figure 9A:
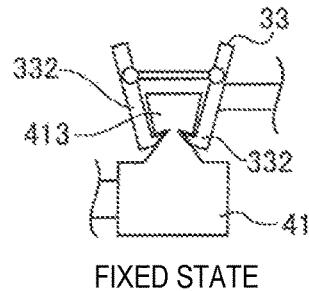
Figure 9B:
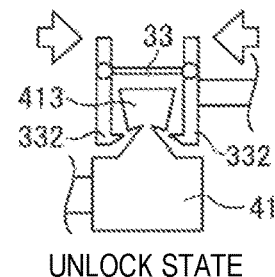
Figure 9C:
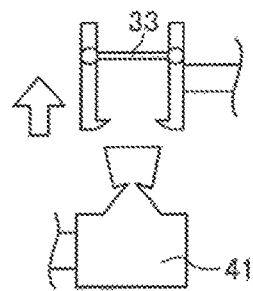

The lock mechanism and the lock release mechanism may have another configuration. For example, the lock mechanism and the lock release mechanism may be configured as illustrated in FIGS. 9A to 9C as a second example. The attachment section 33 includes an engagement section 332 as the second example illustrated in FIGS. 9A to 9C. The mounting section 41 includes an engagement section 413. As illustrated in FIG. 9A, in the fixed state, the engagement section 332 of the attachment section 33 is engaged with the engagement section 413 of the mounting section 41, so that the attachment section 33 is fixed to the mounting section 41 of the display supporting arm 4. Specifically, the engagement section 332 pinches and grips the engagement section 413, to engage with the engagement section 413. The display 3 is thereby fixed to and supported by the display supporting arm 4. In other words, the engagement sections 332 and 413 constitute the lock mechanism to fix the display 3 (the scope or non-scope type display 3a or 3b).

As illustrated in FIG. 9B, when the engagement section 332 is pressed on both sides, the pinching by the engagement section 332 is released, so that the engagement section 332 is disengaged from the engagement section 413. Thus, the fixed state (the locked state) of the attachment section 33 with respect to the mounting section 41 is released. As illustrated in FIG. 9C, when the fixed state is released, the grip sections 32 is operated upward in the vertical direction to dismount the display 3 from the remote control apparatus 100.

Figure 10A:
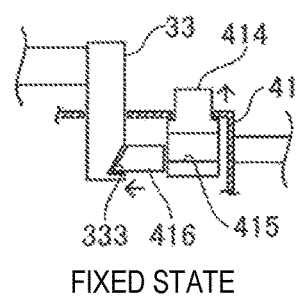

The lock mechanism and the lock release mechanism may have still another configuration. For example, the lock mechanism and the lock release mechanism may have a configuration illustrated in FIGS. 10A to 10C as a third example. The attachment section 33 includes a notch 333 as the third example illustrated in FIGS. 10A to 10C. The mounting section 41 includes a lock release button 414, a fitting section 415, and an engagement section 416. As illustrated in FIG. 10A, the lock release button 414 is energized upward in the vertical direction by a spring or the like. The engagement section 416 is energized in a horizontal direction away from the fitting section 415. The vertical movement of the lock release button 414 and the horizontal movement of the engagement section 416 work in conjunction with a gear and the like.

In the fixed state, the notch 333 of the attachment section 33 is engaged with the engagement section 416 of the mounting section 41, so that the attachment section 33 is fixed to the mounting section 41 of the display supporting arm 4. The display 3 is thereby fixed to and supported by the display supporting arm 4. In other words, the notch 333 and engagement section 416 constitute a lock mechanism to fix the display 3 (the scope or non-scope type display 3a or 3b).

Figure 10B:
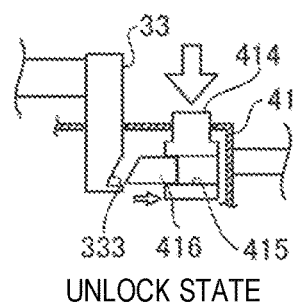

As illustrated in FIG. 10B, when the lock release button 414 is pressed down, the fitting section 415 moves downward. Along with this movements, the engagement section 416 moves toward the fitting section 415 and thus fits into the fitting section 415. The notch 333 thereby disengages from the engagement section 416. The attachment section 33 is thus unfixed (unlocked) from the mounting section 41. In other words, the lock release button 414 functions as a lock release mechanism to release the fixed state by the lock mechanism composed of the notch 333 and engagement section 416. The lock release mechanism releases the fixed state by the lock mechanism by the vertically downward force.

Figure 10C:
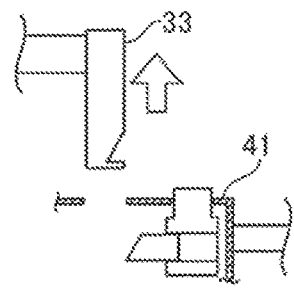

As illustrated in FIG. 10C, in the state where the fixed state is released, the grip section 32 of the display 3 is operated upward in the vertical direction to dismount the display 3 from the remote control apparatus 100.

Having a lower-side larger than an upper-side in size, the engagement section 416 has a slope. When the attachment section 33 is pressed vertically downward against the mounting section 41, the attachment section 33 comes into contact with the slope of the engagement section 416 and presses the engagement section 416 into the fitting section 415 in the horizontal direction. When the attachment section 33 moves to a predetermined position, the engagement section 416 fits into the notch 333 and is locked into the fixed state.

The display supporting arm 4 supports the display 3 as illustrated in FIG. 2. The display supporting arm 4 includes the mounting section 41 and arm sections 42 and 43. At an end of the display supporting arm 4, the mounting section 41 is provided. The other end thereof is supported by a column 44. The column 44 is fixed to a supporting section 91 of the supporting mechanism 9. The display 3 is thus supported by the supporting section 91. The display supporting arm 4 supports the mounting section 41 to be rotatable about the rotation axes A1, A2, and A3, which extend vertically. The mounting section 41 is supported by supporting members including vertical rotation axes so that the angle thereof is adjustable with three degrees of freedom. Specifically, the arm section 43 is supported so as to rotate in a horizontal plane around the rotation axis A1 relative to the column 44. The arm section 42 is supported so as to rotate in a horizontal plane around the rotation axis A2 relative to the arm section 43. The mounting section 41 is supported so as to rotate in a horizontal plane around the rotation axis A3 relative to the arm section 42. With this, the display 3 mounted to the mounting section 41 can be moved in the horizontal direction, to locate the display 3 at a position desired by the operator O.

When the scope type display 3a is mounted on the remote control apparatus 100, as illustrated in FIG. 2, the scope type display 3a can tilt about a horizontal rotation axis B1, which is substantially orthogonal to the rotation axis A3. When the non-scope type display 3b is mounted on the remote control apparatus 100, as illustrated in FIG. 7, the non-scope type display 3b can tilt about a horizontal rotation axis B2, which is substantially orthogonal to the rotation axis A3. This allows adjustments of the angles of elevation and depression of the display 3 attached to the mounting section 41. Note that the positioning of the display supporting arm 4 may be changed manually by the operator O or others or may be changed under movement control by a driver including a motor, an encoder, and a brake.

The armrest 5 is configured to support arms of the operator O. The armrest 5 includes an arm supporting section 51 and a pair of connecting sections 52. The arm supporting section 51 is located in front (on the Y1 side) of the operation handles 1 and is configured to support the arms of the operator O. This stabilizes the arms of the operator O, so that the operator O can stably operate the operation handles 1. Even when the end effectors need to be moved finely, the operator O performs stabilized operation with elbows and the like on the armrest 5. The operator O feels less strain even in long surgery. The arm supporting section 51 extends in the X direction. The pair of connecting sections 52 are provided to both ends of the arm supporting section 51 so as to sandwich the arm supporting section 51 in the X direction. The connecting sections 52 is configured to support the arm supporting section 51. The connecting sections 52 extend in the Y direction. The end of each connecting section 52 on the Y1 side is connected to the arm supporting section 51. The ends of the connecting sections 52 on the Y2 side are connected to the supporting section 91 of the supporting mechanism 9. The armrest 5 is thus supported by the supporting mechanism 9. The connecting sections 52 extend upward from the back (the Y2 side) toward the front (the Y1 side). The connecting sections 52 can be therefore connected to the base 7 at the lower positions, which can stabilize the armrest 5.

As illustrated in FIG. 3, the control apparatus 6 includes, for example, a controller 61 includes a calculator such as a CPU or the like, a storage 62 including a memory, such as a ROM and a RAM, and an image controller 63. The control apparatus 6 may be composed of a single controller performing centralized control or may be composed of plural controllers that perform decentralized control in cooperation with each other. The controller 61 determines whether the action mode instruction inputted by the operation handles 1 is to be executed by the instruments 201a or to be executed by the endoscope 201b, depending on the state of the operation pedal 2. When it is determined that the action mode instruction inputted by the operation handles 1 is to be executed by the instruments 201a, the controller 61 transmits the action mode instruction to the instrument arm 201A. The instrument arms 201A are thereby driven for control of motions of the instruments 201a attached to the instrument arms 201A.

When it is determined that the action mode instruction inputted by the operation handles 1 is to be executed by the endoscope 201b, the controller 61 transmits the action mode instruction to the camera arm 201B. The camera arm 201B is thereby driven for control of motions of the endoscope 201b attached to the camera arm 201B.

The storage 62 stores control programs corresponding to the types of the instruments 201a, for example. The controller 61 reads the stored control programs according to the types of the attached instruments 201a. The action mode instructions from the operation handles 1 and/or the operation pedal 2 of the remote control apparatus 100 thereby causes the respective instruments 201a to perform proper motions.

The image controller 63 transmits an image acquired by the endoscope 201b to the terminal 34 of the display 3. The image controller 63 modifies the image if necessary.

Figure 4:
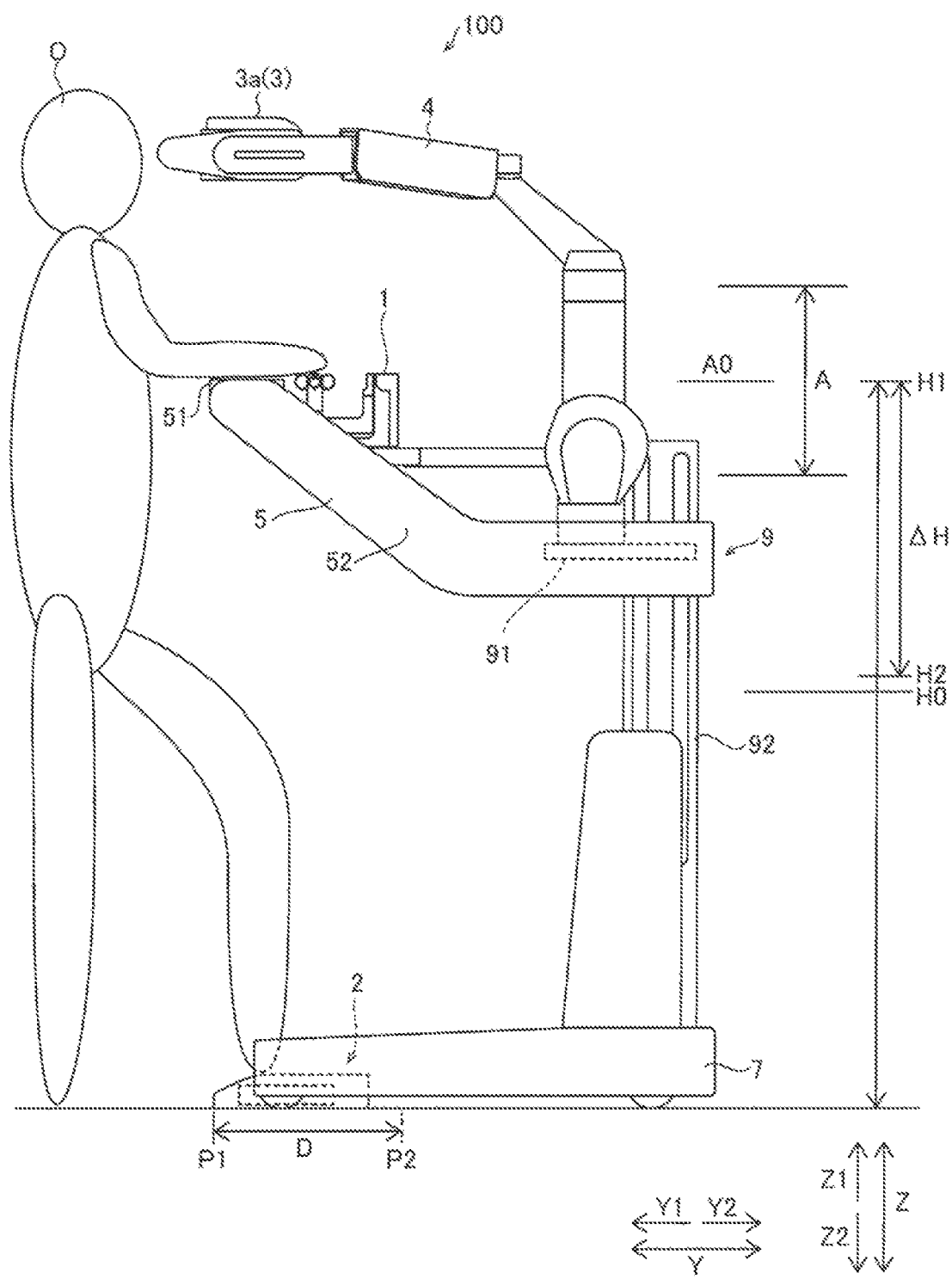
FIG. 4 is a side view illustrating a first mode of the remote control apparatus according to a first embodiment.
Figure 5:
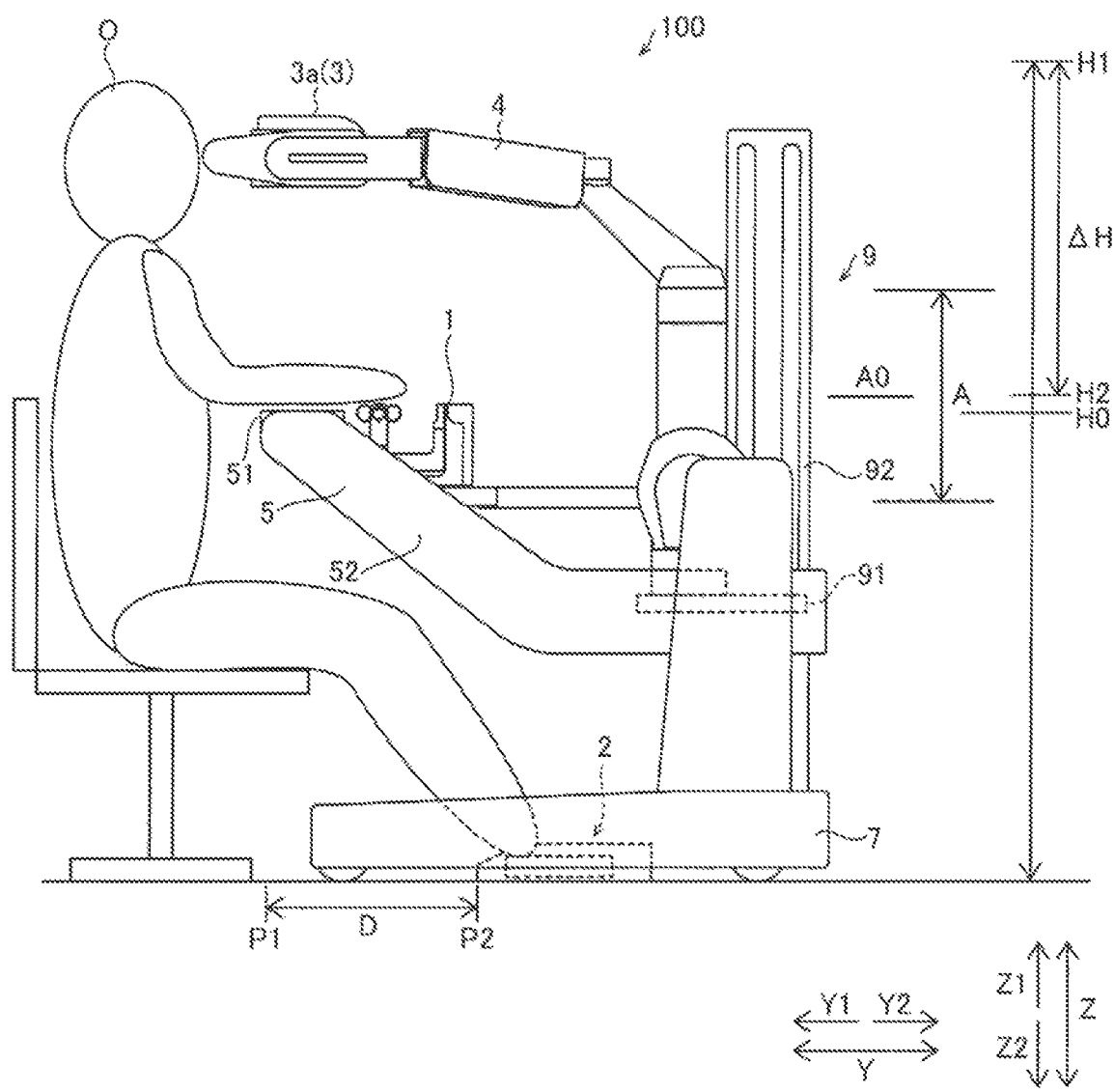
FIG. 5 is a side view illustrating a second mode of the remote control apparatus according to a first embodiment.

Here in a first embodiment, the remote control apparatus 100 is configured such that the operation handles 1 can be moved up and down, as illustrated in FIGS. 4 and 5. Specifically, the posture operation section 8 accepts an operation to move the operation handles 1 up or down. Based on the operation received by the posture operation section 8, the supporting mechanism 9 moves the operation handles 1 up or down.

The supporting mechanism 9 includes the supporting section 91 and a driver 92. The supporting section 91 supports the operation handles 1 and the armrest 5. The supporting section 91 also supports the display 3 through the display supporting arm 4. The driver 92 is configured to move the supporting section 91 up and down. To be specific, the driver 92 includes a motor and an encoder, for example, and moves the supporting section 91 up and down under control by the controller 61. The supporting mechanism 9 may allow the operator O or others to manually change the positioning. In addition, the driver 92 of the supporting mechanism 9 may be driven pneumatically or hydraulically. The armrest 5 may be rotated relative to the supporting mechanism 9 for adjustment of the position. For example, the armrest 5 may be rotated around the rotation axis along the X direction.

In a first embodiment, the supporting mechanism 9 is configured to be transitionable between a first mode and a second mode. In the first mode (see FIG. 4), the operation handles 1 which are positioned at a neutral position A0 of the operation range A are placed and held at a first height position H1, which is 85 cm or more above the floor surface on which the remote control apparatus 100 is installed. In the second mode (see FIG. 5), the operation handles 1 which are positioned at the neutral position A0 of the operation range A are placed and held at a second height position H2, which is 48 cm or more below the first height position H1. With this configuration, when the operation handles 1 which are positioned at the neutral position A0 of the operation range A are located at the first height position H1 (85 cm or more above the floor surface), the operator O is able to operate the operation handles 1 while standing up. When the operation handles 1 which are positioned at the neutral position A0 of the operation range A are located at the second height position H2 (48 cm or more below the first height position H1), the operator O is able to operate the operation handles 1 while sitting down. Accordingly, the operator O is able to operate the remote control apparatus 100 in desired postures.

In addition, since the operation handles 1 are supported by the supporting mechanism 9, the operator O does not need to support the operation handles 1. This suppresses an increase in strain on the operator O. The armrest 5 supporting the arms of the operator O further reduces the strain on the operator O and stabilizes the arms of the operator O. The operator O is therefore able to stably operate the operation handles 1.

Further in a first embodiment, the supporting mechanism 9 is configured to be transitionable between a first mode (see FIG. 4), in which the operation handles 1 are held so that the operation range A of the operation handles 1 is within a clean area set at a predetermined height position or more above the floor surface on which the remote control apparatus 100 is installed, and a second mode (see FIG. 5), in which the operation handles 1 are held so that at least a part of the operation range A of the operation handles 1 is located below the clean area.

In operation rooms, clean operations are used in order to prevent surgical incision sites and medical equipment from being contaminated by pathogen, foreign matters, or the like. In the clean operations, a clean area and a contaminated area, which is other than the clean area, are defined. The area from the floor surface to a certain height position H where foreign matters including dust and grit are more likely to remain is treated as the contaminated area in principle and is eliminated from the clean area. This area lies from the floor surface to a height position of about 70 cm, for example. The clean area is therefore set to a height position of 70 cm or more above the floor surface on which the remote control apparatus 100 is installed, for example. Members of the surgical team including the operator O make sure that only sterile objects are placed in the clean area during surgery and perform sterilization for an object which is to be moved from the contaminated area to the clean area. Similarly, when the members of the surgical team including the operator O locate their hands in the contaminated area, the members sterilize their hands before directly touching objects located in the clean area. The operation handles 1 are treated as unclean objects without sterilization or use of drape, and thus even if the operation handles 1 are located in the clean area, the operator O never accesses the patient P while operating the operation handles 1.

When the operation handles 1 are located so that the operation range A of the operation handles 1 is within the clean area set at the predetermined height or more above the floor surface, the operator O is able to operate the operation handles 1 while keeping his/her hands inside the clean area. Accordingly, if the operation handles 1 are cleaned, for example, the hands of the operator O is kept clean. When the operation handles 1 are held so that at least a part of the operation range A of the operation handles 1 is located below the clean area, the sitting operator O is able to operate the operation handles 1 at the low position. Therefore, the operator O is able to operate the remote control apparatus 100 in desired postures. In addition, the operation handles 1 are supported by the supporting mechanism 9, and the operator O does not need to support the operation handles 1. This can suppress an increase in strain on the operator O.

Further in a first embodiment, the supporting mechanism 9 is configured to allow for transition between a first mode (see FIG. 4), in which the operation handles 1 are held at the position suitable for the operator O to operate the operation handles 1 while standing up and a second mode (see FIG. 5) in which the operation handles 1 are held at the position suitable for the operator O to operate the operation handles 1 while sitting down. When the remote control apparatus 100 is set to the first mode, the operator O can operate the operation handles 1 while standing up. When the remote control apparatus 100 is set to the second mode, the operator O is able to operate the operation handles 1 while sitting down. The operator O is thus able to operate the remote control apparatus 100 in desired postures. In addition, the operation handles 1 are supported by the supporting mechanism 9, and the operator O does not need to support the operation handles 1. This can reduce an increase in strain on the operator O.

Further, the supporting mechanism 9 is configured to move both the operation handles 1 and the armrest 5 up and down between the first and second modes. Specifically, the supporting mechanism 9 is configured to integrally move the operation handles 1 and armrest 5 up and down between the first and second modes. This requires less components than that in the case where members for moving the operation handles 1 and the armrest 5 up and down are separately provided. It is therefore possible to simplify the apparatus configuration and suppress an increase in size of the apparatus. In addition, the supporting mechanism 9 is configured to also move the display 3 supported by the display supporting arm 4 up and down between the first and second modes. The supporting mechanism 9 is thus configured to integrally move the operation handles 1, the armrest 5, and the display 3 up and down between the first and second modes.

In other words, the supporting mechanism 9 supports the display 3 that displays an image captured by the endoscope 201*b* and supports the display 3 so that the position of the display 3 relative to the operation handles 1 is changeable in each of the first and second modes. To be specific, the position of the display 3 is moved relative to the operation handles 1 by the display supporting arm 4 supported by the supporting mechanism 9. The position of the display 3 relative to the operation handles 1 can be therefore changed according to the physique and posture of the operator O. This can increase the versatility of the display 3.

The posture operation section 8 is configured to accept operations to move the operation handles 1, the display 3 supported by the display supporting arm 4, and the armrest 5 up and down. The posture operation section 8 is also configured to accept operations to move the operation pedal 2 forward and backward (in the Y direction). The posture operation section 8 thus accepts operations to transform the remote control apparatus 100 between first and second postures.

In other words, the posture operation section 8 is an operating section capable of inputting a posture change instruction to change the posture of the remote control apparatus 100 between the standing position (first posture) and the sitting position (second posture). The posture operation section 8 includes plural operation buttons.

The supporting mechanism 9 is configured to move up and down, the operation handles 1, the display 3 supported by the display supporting arm 4, and the armrest 5. The driver 92 of the supporting mechanism 9 includes a motor and an encoder, for example and is driven based on instructions from the posture operation section 8. That is, the supporting mechanism 9 is configured to move, in response to the posture change instruction inputted through the posture operation section 8, the operation handles 1 between the first mode and the second mode. The driver 92 is supported on the base 7. The driver 92 is provided near the Y2-side end of the base 7 in the front-back direction (in the Y direction) and is located at the substantially center of the base 7 in the right-left direction (in the X direction). The handles 1, the display 3 supported by the display supporting arm 4, and the armrest 5 may be independently moved up and down by the supporting mechanism 9.

In the first mode, the supporting mechanism 9 preferably holds the operation handles 1 positioned at the neutral position A0 of the operation range A, at a first height position H1 of 99 cm or more above the floor surface on which the remote control apparatus 100 is installed. In the second mode, the supporting mechanism 9 preferably holds the operation handles 1 positioned at the neutral position A0 of the operation range A, at a second height position H2, which is 50 cm or more below the first height position H1.

Further the remote control apparatus is configured to disable operations of the surgical manipulator 201 through the operation handles 1 at transformation between the first and second modes. To be specific, during transformation between the first and second modes, operation by the operation handles 1 is disabled, or transmission of action mode instructions is disabled. In other words, during transformation between the first and second modes, the controller 61 does not transmit an action mode instruction to the surgical manipulator 201 even if the action mode instruction is transmitted from the operation handles 1. This prevents the surgical manipulator 201 from moving when the operation handles 1 are operated accidentally during transformation between the first and second modes.

As illustrated in FIG. 4, when the remote control apparatus 100 is in the standing position (the first posture), the operation handles 1 are positioned at a height suitable for the standing operator O to grip the operation handles 1 positioned at the neutral position A0 with the arms bent at substantially right angles. The display 3 is positioned at a height suitable for the standing operator O to look at the display 3. For example, in a case where the scope type display 3*a* is mounted, the scope type display 3*a* is set at the same height as the eyes of the operator O.

When the area from the floor surface to a height position H of 70 cm is set to the contaminated area in a surgery room, the operation range A of the operation handles 1 is fully within the clean area 70 cm or more above the floor surface in the standing position mode (the first posture) by designing based on a human model for ergonomics.

When the remote control apparatus 100 is in the standing position (the first posture), the operation pedal 2 is moved to a position P1 in the front side (in the Y1 side) of the remote control apparatus 100. In other words, the operation pedal 2 is located to such a position that the standing operator O reaches the operation pedal 2 with his/her foot while touching the operation handles 1 with his/her hands.

As illustrated in FIG. 5, when the remote control apparatus 100 is in the sitting position (the second posture). The operation handles 1 are positioned at a height suitable for the operator O sitting in the chair to grip the operation handles 1 positioned at the neutral position A0 with his/her arms bent at substantially right angles. In addition, the display 3 is positioned at a height position suitable for the operator O sitting in the chair to look at the display 3. For example, when the scope type display 3a is mounted, the scope type display 3a is set at the same height as the eyes of the operator O. With the remote control apparatus 100, the operator O can execute surgery while sitting down in a long surgery. This can reduce fatigue of the operator O.

When the area from the floor surface to the height position H of 70 cm is set to the contaminated area in a surgery room, at least a part of the operation range A of the operation handles 1 is in the contaminated area in the sitting position mode (the second posture) by designing based on human models for ergonomics.

When the remote control apparatus 100 is in the sitting position (the second posture), the operation pedal 2 is moved to a position P2 in the back side (in the Y2 side) of the remote control apparatus 100. In other words, the operation pedal 2 is located to such a position that the sitting operator O reaches the operation pedal 2 with his/her feet while touching the operation handles 1 with his/her hands. For example, the operation pedal 2 is configured to be movable forward and backward by 300 mm or more (in the Y direction). Preferably, the operation pedal 2 is configured to be movable forward and backward by 350 mm or more (in the Y direction). With this, the operation pedal 2 can be easily located to the positions suitable for the first and second postures.

Specific dimensions and the like of the remote control apparatus 100 are designed using measurement data described in "1988 ANTHROPOMETRIC SURVEY OF U. S. ARMY PERSONNEL: METHODS AND SUMMARY STATISTICS (1988)".

The remote control apparatus 100 may be designed with reference to JIS standards. For example, "JIS Z8503-4: 2006 (ISO 11064-4: 2004), Ergonomic design of control centers, Part 4: Layout and dimensions of workstations" prescribes use of the 5th and 95th percentile human models.

The operation range A is defined as a region between 15 cm above and below the neutral position A0. That is, the dimension of the operation range A in the height direction is defined as 30 cm. The operation range A is defined based on the dimensions of the motion range of surgical tools set to keep good operability of the surgical tools at laparoscopic surgery and the motion scaling ratio of the operation handles 1. The set motion range of the surgical tools has a dimension of 30 cm in the height direction, and the motion scaling ratio of the operation handles 1 is 1/2. The dimension of the operation range A in the height direction is therefore 30 cm based on the dimension of the motion range of the surgical tools in the height direction and the motion scaling ratio of the operation handles 1.

Figure 6A:
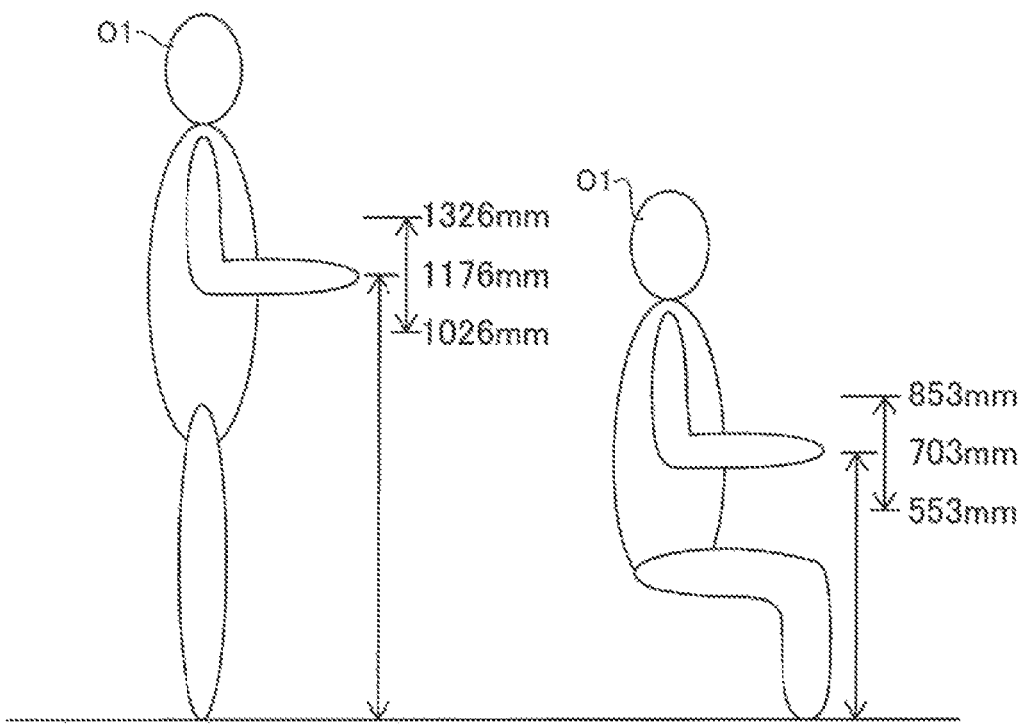
FIG. 6A is a view illustrating a model of large operators O1.
Figure 6B:
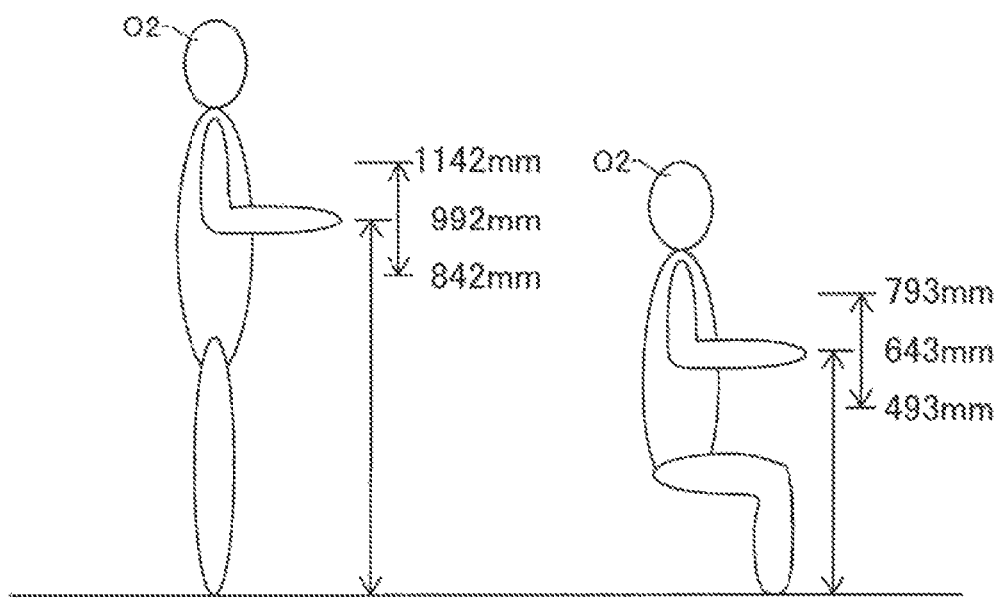
FIG. 6B is a view illustrating a model of small operators O2.

FIG. 6A illustrates a model of large operators O1, and FIG. 6B illustrates a model of small operators O2.

In FIG. 6A, the model of the large operators O1 is based on body data of German men. When the fifth largest model among 100 German male models selected at random stands and grips the operation handles 1 positioned at the neutral position A0 of the operation range A with his arms bent at right angles, the height position of the operation handles 1 is about 1176 mm, and the lower and upper limits of the height position of the operation range A are about 1026 mm and 1326 mm, respectively. On the other hand, when the fifth largest model sits down and grips the operation handles 1 positioned at the neutral position A0 of the operation range A with his arms bent at right angles, the height position of the operation handles 1 is about 703 mm, and the lower and upper limits of the height position of the operation range A are about 553 mm and about 853 mm, respectively.

In FIG. 6B, the model of the small operators O2 is based on body data of Japanese women. When the fifth smallest model among 100 Japanese female models selected at random stands and grips the operation handles 1 positioned at the neutral position A0 of the operation range A with her arms bent at right angles, the height position of the operation handles 1 is about 992 mm, and the lower and upper limits of the height position of the operation range A are about 842 mm and about 1142 mm, respectively. On the other hand, when the fifth smallest model sits down and grips the operation handles 1 positioned at the neutral position A0 of the operation range A with her arms bent at right angles, the height position of the operation handles 1 is about 643 mm, and the lower and upper limits of the height position of the operation range A are about 493 mm and about 793 mm, respectively.

Based on the aforementioned data, the height position of the operation handles 1 that allows plural operators O having different types of physique to take standing and sitting positions without any problem is as follows. First, the height position of the operation handles 1 positioned at the neutral position A0 of the operation range A in the standing position mode (the first mode) is preferably set to about 99 cm or more corresponding to the standing model of the small operators O2. This allows most operators O to comfortably operate the operation handles 1 while standing. With this, regarding the operation handles 1 configured to move down by 15 cm from the neutral position A0, the lower limit of the height position of the operation range A of the operation handles 1 in the standing position mode is 84 cm or more as described above.

Further, the height position of the operation handles 1 positioned at the neutral position A0 in the standing position mode (the first mode) is preferably set to about 85 cm or more. With this, regarding the operation handles 1 configured to move down by 15 cm from the neutral position A0, the lower limit of the height position of the operation range A of the operation handles 1 in the standing position mode is higher than 70 cm, and the operation range A of the operation handles 1 is therefore within the clean area. Since the lower limit of the height position of the operation range A corresponding to the standing model of the small operators O2 is about 84 cm, setting the lower limit of the height position of the operation range A to 70 cm allows more operators O having different types of physiques to comfortably operate the operation handles 1 while standing up.

Next, the height position of the operation handles 1 positioned at the neutral position A0 of the operation range A in the sitting position mode (the second mode) is preferably set to about 64 cm or more corresponding to the sitting model of the small operators O2. This allows most operators O to comfortably operate the operation handles 1 while sitting down.

Next, the displacement (adjustment width) of the height position of the operation handles 1 at transition of the remote control apparatus 100 between the standing position mode and the sitting position mode is preferably set to about 35 cm or more. This is the difference between the height (about 99 cm) of the operation handles 1 positioned at the neutral position A0 corresponding to the standing model of the small operators O2 and the height (about 64 cm) of the operation handles 1 positioned at the neutral position A0 corresponding to the sitting model of the small operators O2.

In addition, the displacement of the height position of the operation handles 1 at transition of the remote control apparatus 100 between the standing position mode and the sitting position mode is preferably set to about 48 cm or more. This is the difference between the height (about 118 cm, the maximum height of the operation handles 1 positioned at the neutral position A0 in the standing position mode in this example) of the operation handles 1 positioned at the neutral position A0 corresponding to the standing model of the large operators O1 and the height (about 70 cm) of the operation handles 1 positioned at the neutral position A0 corresponding to the sitting model of the large operators O1.

As described above, the adjustment width of the height position of the operation handles 1 at transition between the standing position mode and the sitting position mode is greater than the adjustment width desirably set so as to fit to the different types of physique of the operators O in the standing position mode (about 19 cm as the difference between the height position of the operation handles 1 positioned at the neutral position A0, corresponding to the model of the large operators O1 and the height position of the operation handles 1 positioned at the neutral position A0, corresponding to the model of the small operators O2, for example) and the adjustment width desirably set so as to fit to the different types of physique of the operators O in the sitting position mode (about 6 cm as the difference between the height position of the operation handles 1 positioned at the neutral position A0 corresponding to the model of the large operators O1 and the height position of the operation handles 1 positioned at the neutral position A0 corresponding to the model of the small operators O2, for example).

Note that if the positions of the operation handles 1 are set higher than about 118 cm (the height position of the operation handles 1 positioned at the neutral position A0 corresponding to the standing model of the large operators O1), the above-described adjustment width is further increased. It is then preferable that the adjustment width is 50 cm or more from the height position of the operation handles 1 in the standing position mode. Furthermore, the displacement of the height position of the operation handles 1 at transition of the remote control apparatus 100 between the standing position mode and the sitting position mode is preferably set to about 54 cm or more, which is the difference between the height (about 118 cm) of the operation handles 1 positioned at the neutral position A0 corresponding to the standing model of the large operators O1 and the height (about 64 cm) of the operation handles 1 positioned at the neutral position A0 corresponding to the sitting model of the small operators O2. As for definition of the operation range A, the design of the operation range A may be modified by considering the size of the operation handles 1 and the like. Although the vertical width of the operation range A is assumed to be 30 cm, the vertical width thereof may be set to 20, 25, or 35 cm, for example.

Second Embodiment

Figure 11:
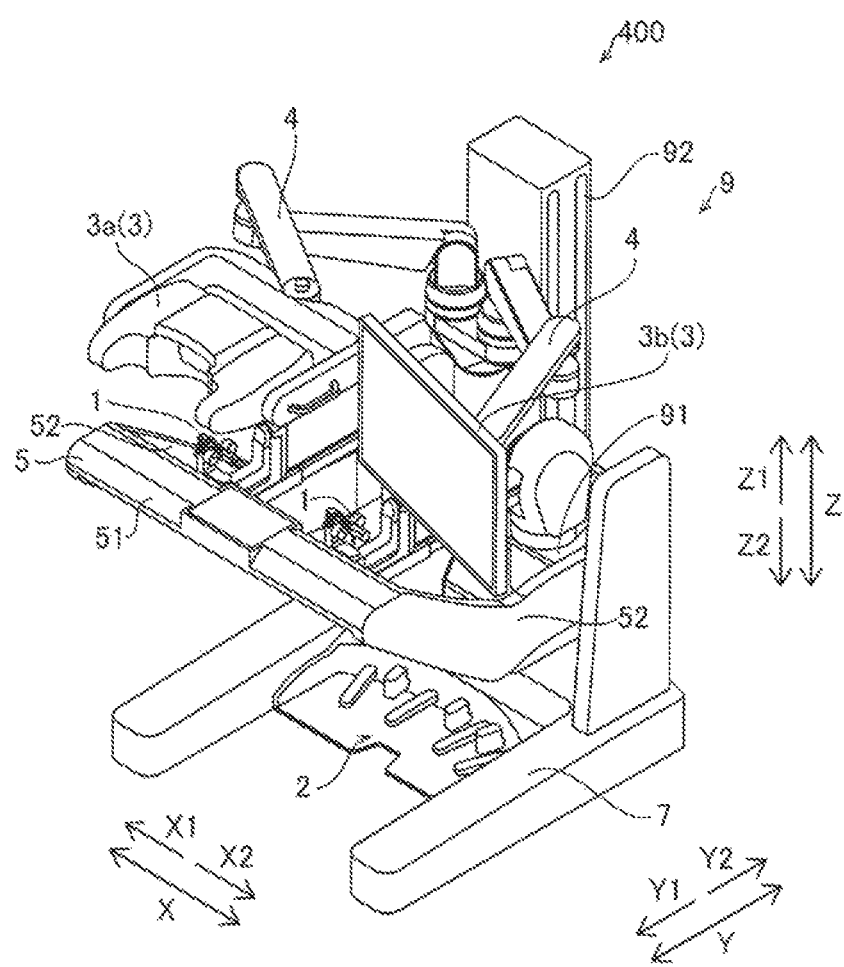
FIG. 11 is a view illustrating a remote control apparatus according to a second embodiment.

Next, with reference to FIG. 11, a second embodiment of the disclosure is described. In a second embodiment, description is given of an example of the configuration of a remote control apparatus including plural displays, which is different from a first embodiment in which the remote control apparatus includes one display.

As illustrated in FIG. 11, a remote control apparatus 400 according to a second embodiment includes plural displays 3. In the example illustrated in FIG. 11, both the scope type display 3*a* and non-scope type display 3*b* as the displays 3 are mounted on the remote control apparatus 400. The two displays 3 are placed side by side in the right-left direction (in the X direction).

In other words, the remote control apparatus 400 includes plural (two) mounting sections 41. Specifically, the remote control apparatus 400 includes plural (two) display supporting arms 4. The mounting sections 41 are provided at the distal ends of the respective display supporting arms 4. This allows both of the scope and non-scope type displays 3*a* and 3*b* to be mounted on the remote control apparatus 400, thus effectively increasing the versatility of the displays 3.

Here in a second embodiment, the supporting mechanism 9 is configured to be transitionable between the first mode and the second mode. In the first mode, the operation handles 1 which are positioned at the neutral position A0 of the operation range A are placed and held at the first height position H1, which is 85 cm or more above the floor surface on which the remote control apparatus 400 is installed. In the second mode, the operation handles 1 which are positioned at the neutral position A0 of the operation range A are placed and held at the second height position H2, which is 48 cm or more below the first height position H1. In other words, the supporting mechanism 9 is configured to be transitionable between the first mode in which the operation handles 1 are held such that the operation range A of the operation handles is positioned within the clean area set at the predetermined height position or more above the floor surface on which the remote control apparatus 400 is installed, and the second mode in which the operation handles 1 are held such that t at least a part of the operation range A of the operation handles 1 is located below the clean area. That is, the supporting mechanism 9 is configured to be transitionable between the first mode in which the operation handles 1 are held in the position suitable for the operator O to operate the operation handles in the standing posture and the second mode in which the operation handles 1 are held in the position suitable for the operator O to operate the operation handles 1 in the sitting posture. With this configuration, the operator O can operate the remote control apparatus 400 in desired postures. Further, since the operation handles 1 are supported by the supporting mechanism 9, the operator O does not need to support the operation handles 1. This can suppress increase of the burden on the operator O. Further, the armrest 5 to support the arms of the operator can reduce the burden on the operator O and stabilize the arm of the operator O. The operator O is therefore able to stably operate the operation handles 1.

The non-scope type display 3*b*, which is one of the displays 3, displays at least one of a previously acquired image of the surgical site, information indicating the state of the surgery, and operation information. For example, the non-scope type display 3*b* displays X-ray images or magnetic resonance images previously captured. The other scope type or non-scope type display displays a 3D image acquired from the endoscope. This further increases the versatility and expandability such that the operator O performs surgery by mainly looking at the endoscopic image on the other display, while viewing, as needed, at least one kind of auxiliary information among the image of the surgery site previously acquired, the information indicating the state of the surgery, and the operation information.

As described above, the remote control apparatus 400 according to a second embodiment is configured such that the scope or non-scope type display 3*a* or 3*b* is selectively and detachably mounted as a main display 3 and the non-scope type display 3*b* is mounted on the remote control apparatus 400 as an auxiliary display. With this configuration, the operator O can select one of the immersive remote control apparatus and the open-type remote control apparatus and look at the auxiliary information during surgery. Since the remote control apparatus 400 is provided with the plural mounting sections, it is possible to freely select on which side the main display is installed.

In the example of FIG. 11, the scope type display 3a and non-scope type display 3b are attached to the two mounting sections 41. However, the scope type display 3a may be attached to each of the two mounting sections 41, or the non-scope type display 3b may be attached to each of the two mounting sections 41.

Note that the other configurations according to a second embodiment are the same as or similar to those of a first embodiment.

Third Embodiment

Figure 12:
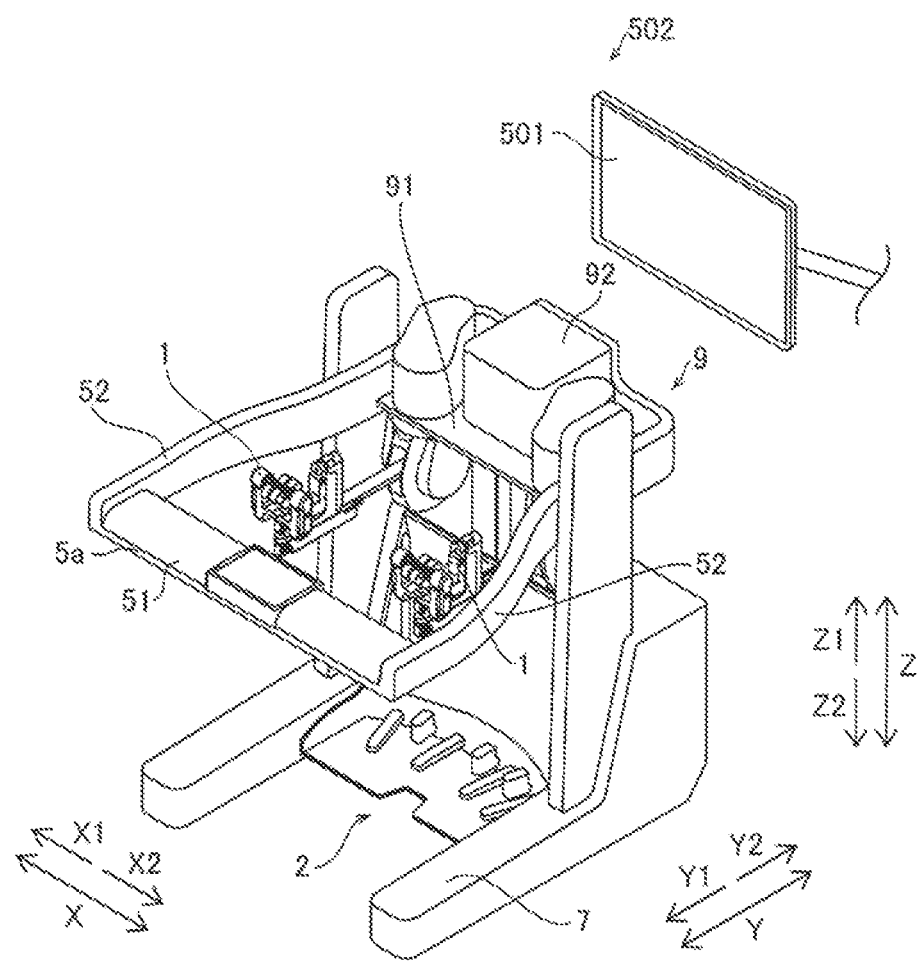
FIG. 12 is a view illustrating a remote control apparatus according to a third embodiment.

Next, with reference to FIG. 12, a third embodiment of the disclosure is described. In a third embodiment, description is given of a configuration example in which a display apparatus is provided separately from a remote control apparatus, which is different from first and second embodiments in which the remote control apparatus includes the display.

In a third embodiment, as illustrated in FIG. 12, a display apparatus 501 is provided separately from a remote control apparatus 500. That is, a display is not attached to the remote control apparatus 500. In addition, the remote control apparatus 500 does not include a display supporting arm that is configured to support a display. The remote control apparatus 500 and the display apparatus 501 provided outside of the remote control apparatus 500 constitute a remote control system 502. The configuration of the remote control apparatus 500 is thereby simplified.

In a third embodiment, the supporting mechanism 9 is configured to be transitionable between the first mode and the second mode. In the first mode, the operation handles 1 which are positioned at the neutral position A0 of the operation range A are placed and held at the first height position H1, which is 85 cm or more above the floor surface on which the remote control apparatus 500 is installed. In the second mode, the operation handles 1 which are positioned at the neutral position A0 of the operation range A are placed and held at the second height position H2, which is 48 cm or more below the first height position H1. In other words, the supporting mechanism 9 is configured to be transitionable between the first mode in which the operation handles 1 are held such that the operation range A of the operation handles is positioned within the clean area set at the predetermined height position or more above the floor surface on which the remote control apparatus 500 is installed, and the second mode in which the operation handles 1 are held such that t at least a part of the operation range A of the operation handles 1 is located below the clean area. That is, the supporting mechanism 9 is configured to be transitionable between the first mode in which the operation handles 1 are held in the position suitable for the operator O to operate the operation handles in the standing posture and the second mode in which the operation handles 1 are held in the position suitable for the operator O to operate the operation handles 1 in the sitting posture. With this configuration, the operator O can operate the remote control apparatus 500 in desired postures. Further, since the operation handles 1 are supported by the supporting mechanism 9, the operator O does not need to support the operation handles 1. This can suppress increase of the burden on the operator O. Further, the armrest 5 to support the arms of the operator can reduce the burden on the operator O and stabilize the arms of the operator O. The operator O is therefore able to stably operate the operation handles 1.

The supporting mechanism 9 is configured to move both of the operation handle 1 and the armrest 5a in the upward direction and the downward direction between the first mode and the second mode.

The connecting sections 52 of the armrest 5 has a shape extending substantially in the horizontal direction (the Y direction). This can ensure an appropriate size of a legroom for the feet of the operator O.

The display apparatus 501 is installed in front (on the Y2 side) of the remote control apparatus 500. That is, the display apparatus 501 is placed in such a position that the operator O who is operating the remote control apparatus 500 is able to look at the screen. The display apparatus 501 includes a display apparatus such as a liquid crystal display, an organic EL display, or a plasma display, and displays 2D or 3D images captured by the endoscope 201b. The display apparatus 501 may display at least one of a previously acquired image of the surgery site, information representing the surgery state, and operation information. For example, the display apparatus 501 displays X-ray images or magnetic resonance images previously acquired.

Note that the other configurations according to a third embodiment are the same as or similar to those of a first embodiment.

(Modification)

It should be understood that the disclosed embodiments are shown by way of example in every respect and are not limitative. The scope of the disclosure is not determined by the aforementioned embodiments but is specified by Claims. The scope of the disclosure includes all alternations (modifications) within meanings and scope equivalent to the scope of Claims.

For example, the aforementioned first and second embodiments disclose examples of the configuration in the connecting sections 52 of the armrest 5 extends upwardly toward the front (the side where the operator O is located, in the Y1 direction). The aforementioned third embodiment disclose an example of the configuration in the connecting sections 52 of the armrest 5a extend in the horizontal direction. However, the disclosure is not limited to those examples. For example, as illustrated in a modification of FIG. 13, the connecting sections 52 of an armrest 5b may extend downwardly toward the front. This forms a large space at the feet of the operator O.

Figure 13:
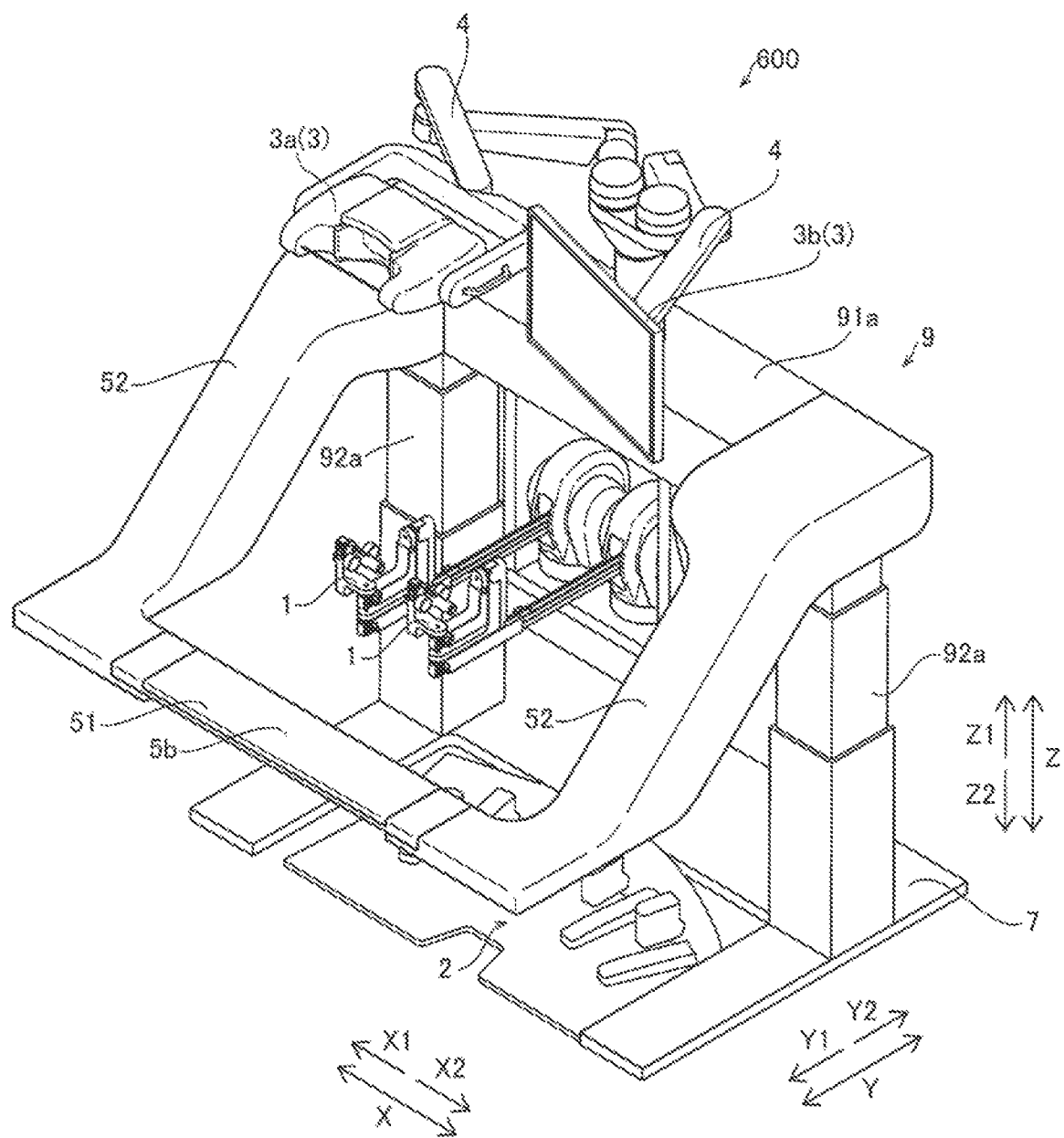
FIG. 13 is a view illustrating a remote control apparatus according to a modification of the first to third embodiments.

The aforementioned first to third embodiments disclose examples of the configuration in which the one supporting mechanism 9 is provided substantially at the center of the remote control apparatus in in the right-left direction (the X direction), to move the operation handles 1 and armrest 5 up and down. However, the disclosure is not limited to those examples. As illustrated in the modification of FIG. 13, a supporting mechanism 9a that supports the operation handles 1 and the armrest 5 may be provided at both ends of a remote control apparatus 600 in the right-left direction (the X direction). For example, the supporting mechanism 9a may include a supporting section 91a and a pair of drivers 92a that is arranged at the right and left ends and supports the supporting section 91a. The pair of drivers 92a expand and contract in synchronization to move the supporting section 91a up and down.

The aforementioned first embodiment discloses an example of the configuration in which the remote control apparatus 100 is provided with one mounting section 41 to which the display 3 is attachable. The aforementioned second embodiment discloses an example of the configuration in which the remote control apparatus is provided with the two mounting sections 41 to which the displays 3 are attachable. The disclosure is not limited to those examples. For example, the remote control apparatus may be provided with three or more mounting sections 41.

The aforementioned first to third embodiments disclose examples of the configurations in which the mounted display is connected to the remote control apparatus with a cable so as to exchange information with the same. The disclosure is not limited to these examples. For example, the mounted display is connected to the remote control apparatus so as to exchange information through wireless communication.

The aforementioned first to third embodiments disclose examples of the configuration in which the supporting mechanism moves the operation handles and the armrest up and down. However, the disclosure is not limited to these examples. For example, the supporting mechanism may move the operation handles and the armrest in the horizontal direction in addition to up and down movements.

The invention claimed is:

1. A remote control apparatus comprising:
   a display configured to display an image captured by an endoscope;
   a pair of left and right operation handles separated away from each other in a left-right direction, wherein each of the pair of operation handles is configured to be movable within a predetermined operation range and to remotely operate medical equipment;
   an armrest to support arms of an operator; and
   a supporting mechanism that includes: a supporting section supporting the display, the pair of operation handles, and the armrest such that each of the pair of operation handles hangs down from the supporting section; and a driver including a motor configured to move the supporting section up-and-down along the driver in a vertical direction, wherein
   the supporting mechanism is configured to be transitionable between a first mode in which each operation handle that is positioned at a neutral position of the operation range is held at a first height position, which is 85 cm or more above a floor surface on which the remote control apparatus is placed and a second mode in which each operation handle that is positioned at the neutral position of the operation range is held at a second height position, which is 48 cm or more below the first height position, and
   the supporting mechanism moves, in response to a posture change instruction to transition between the first mode and the second mode, the supporting section along the driver in the vertical direction by the motor of the driver to move the display, the pair of operation handles, and the armrest in an integrated manner in the vertical direction.

2. The remote control apparatus according to claim 1, further comprising a posture operation section configured to allow a user to input the posture change instruction, wherein
   the driver drives in response to the posture change instruction input through the posture operation section.

3. The remote control apparatus according to claim 1, wherein
   the supporting mechanism holds the pair of operation handles in such a manner that, in the first mode, each operation handle that is positioned at the neutral position of the operation range is held at the first height position which is 99 cm or more above the floor surface on which the remote control apparatus is placed.

4. The remote control apparatus according to claim 1, wherein
   the supporting mechanism holds the pair of operation handles in such a manner that, in the second mode, each operation handle that is positioned at the neutral position of the operation range is held at the second height position which is 50 cm or more below the first height position.

5. The remote control apparatus according to claim 1, wherein
   the armrest includes an arm supporting section extending in a left-right direction and a pair of connecting sections extending from left and right end portions of the arm supporting section in a front-back direction,
   the supporting section of the supporting mechanism supports the pair of connecting sections of the armrest at left and right end portions of the supporting section and supports the display at an upper portion of the supporting section.

6. The remote control apparatus according to claim 1, wherein
   the driver is formed to extend in the vertical direction and is configured to move the supporting section along the vertical direction.

7. A remote control system comprising:
   the remote control apparatus according to claim 1; and
   a display apparatus provided outside of the remote control apparatus.

8. A remote control apparatus comprising:
   a display configured to display an image captured by an endoscope;
   a pair of left and right operation handles separated away from each other in a left-right direction, wherein each of the pair of operation handles is configured to be movable within a predetermined operation range and to remotely operate medical equipment;
   an armrest to support arms of an operator; and
   a supporting mechanism that includes: a supporting section supporting the display, the pair of operation handles, and the armrest such that each of the pair of operation handles hangs down from the supporting section; and a driver including a motor configured to move the supporting section up-and-down along the driver in a vertical direction, wherein
   the supporting mechanism is configured to be transitionable between a first mode in which each operation handle is held such that the operation range of the operation handle is within in a clean area set at a predetermined height position or more above a floor surface on which the remote control apparatus is placed, and a second mode in which each operation handle is held such that at least a part of the operation range of the operation handle is located below the clean area, and
   the supporting mechanism moves, in response to a posture change instruction to transition between the first mode and the second mode, the supporting section along the driver in the vertical direction by the motor of the driver to move the display, the pair of operation handles, and the armrest in an integrated manner in the vertical direction.

9. The remote control apparatus according to claim 8, further comprising
   a posture operation section configured to allow a user to input the posture change instruction, wherein the driver drives in response to the posture change instruction input through the posture operation section.

10. The remote control apparatus according to claim 8, wherein
the clean area is set at a position of 70 cm or more above the floor surface on which the remote control apparatus is placed.

11. The remote control apparatus according to claim 8, wherein
a lower limit of the height position of the operation range of the operation handle in the second mode is 48 cm or more below a lower limit of the height position of the operation range of the operation handle in the first mode.

12. A remote control system comprising:
the remote control apparatus according to claim 8; and
a display apparatus provided outside of the remote control apparatus.

13. A remote control apparatus comprising:
a display configured to display an image captured by an endoscope;
a pair of left and right operation handles separated away from each other in a left-right direction, wherein each of the pair of operation handles is configured to be movable within a predetermined operation range and to remotely operate medical equipment;
an armrest to support arms of an operator; and
a supporting mechanism that includes: a supporting section supporting the display, the pair of operation handles, and the armrest such that each of the pair of operation handles hangs down from the supporting section; and a driver including a motor configured to move the supporting section up-and-down along the driver in a vertical direction, wherein
the supporting mechanism is configured to be transitionable between a first mode in which each operation handle is held at a position suitable for the operator to operate the operation handle at a standing posture and a second mode in which each operation handle is held at a position suitable for the operator to operate the operation handle in a sitting posture, and
the supporting mechanism moves, in response to a posture change instruction to transition between the first mode and the second mode, the supporting section along the driver in the vertical direction by the motor of the driver to move the display, the pair of operation handles, and the armrest in an integrated manner in the vertical direction.

14. The remote control apparatus according to claim 13, further comprising
a posture operation section configured to allow a user to input the posture change instruction, wherein
the driver drives in response to the posture change instruction input through the posture operation section.

15. The remote control apparatus according to claim 13, wherein
the armrest includes: an arm supporting section to support the arms of the operator; and a pair of connecting sections connected to the arm supporting section and extending in a front-back direction along a horizontal direction.

16. The remote control apparatus according to claim 13, wherein
the armrest includes: an arm supporting section to support the arms of the operator; and a pair of connecting sections connected to the arm supporting section, wherein each of the pair of connecting sections extends in a front-back direction such that each of the pair of connecting sections extends downwardly toward the front side.

17. The remote control apparatus according to claim 13, wherein
the armrest includes: an arm supporting section to support the arms of the operator; and a pair of connecting sections connected to the arm supporting section, wherein each of the pair of connecting sections extends in a front-back direction such that each of the pair of connecting sections extends upwardly toward the front side.

18. The remote control apparatus according to claim 13, wherein
the display comprises an open-type display that includes a flat screen.

19. The remote control apparatus according to claim 13, wherein
the display comprises a scope type display.

20. The remote control apparatus according to claim 13, wherein,
the supporting mechanism includes a mounting section to which a scope type display and a non-scope type display are selectively mountable as the display.

21. The remote control apparatus according to claim 13, wherein
the remote control apparatus is configured, during transformation between the first mode and the second mode, to disable operations of the medical equipment by the operation handle.

22. A remote control system comprising:
the remote control apparatus according to claim 13; and
a display apparatus provided outside of the remote control apparatus.

23. A remote control apparatus comprising:
a display configured to display an image captured by an endoscope;
a pair of left and right operation handles separated away from each other in a left-right direction, wherein each of the pair of left and right operation handles is configured to be movable within a predetermined operation range and to remotely operate medical equipment;
an armrest to support arms of an operator;
a supporting mechanism that includes: a supporting section; and a driver including a motor configured to move the supporting section up-and-down in a vertical direction; and
a pair of left and right handle support arms directly or indirectly connected to the supporting section, extending in a rear direction, and respectively supporting the pair of left and right operation handles, wherein
the supporting section of the supporting mechanism supports the display, the pair of left and right handle support arms, and the armrest,
the supporting mechanism is configured to be transitionable between a first mode in which each operation handle that is positioned at a neutral position of the operation range is held at a first height position, which is 85 cm or more above a floor surface on which the remote control apparatus is placed and a second mode in which each operation handle that is positioned at the neutral position of the operation range is held at a second height position, which is 48 cm or more below the first height position, and
the supporting mechanism moves, in response to a posture change instruction to transition between the first mode and the second mode, the supporting section in the vertical direction by the motor of the driver to move the display, the pair of left and right operation handles, and the armrest in an integrated manner in the vertical direction.

* * * * *

UNITED STATES PATENT AND TRADEMARK OFFICE
CERTIFICATE OF CORRECTION

| | |
|---|---|
| PATENT NO. | : 11,529,200 B2 |
| APPLICATION NO. | : 16/699735 |
| DATED | : December 20, 2022 |
| INVENTOR(S) | : Kazuki Ishihara, Tetsuya Nakanishi and Shiro Horita |

It is certified that error appears in the above-identified patent and that said Letters Patent is hereby corrected as shown below:

On the Title Page

Item (73) The Incorrect Assignee Name listed:
MEDICARON CORPORATION

The Correct Assignee Name is as follows:
MEDICAROID CORPORATION

Signed and Sealed this
Twenty-eighth Day of February, 2023

Katherine Kelly Vidal
*Director of the United States Patent and Trademark Office*